United States Patent
Demeester et al.

(10) Patent No.: US 9,535,145 B2
(45) Date of Patent: Jan. 3, 2017

(54) MR-PET CYCLIC MOTION GATING AND CORRECTION

(75) Inventors: Gordon D. Demeester, Wickliffe, OH (US); Michael A. Morich, Mentor, OH (US); Timothy P. Eagan, Shaker Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1800 days.

(21) Appl. No.: 12/740,358

(22) PCT Filed: Oct. 29, 2008

(86) PCT No.: PCT/IB2008/054488
§ 371 (c)(1),
(2), (4) Date: Apr. 29, 2010

(87) PCT Pub. No.: WO2009/060348
PCT Pub. Date: May 14, 2009

(65) Prior Publication Data
US 2010/0290683 A1   Nov. 18, 2010

Related U.S. Application Data

(60) Provisional application No. 60/986,699, filed on Nov. 9, 2007.

(51) Int. Cl.
*G06Q 10/00* (2012.01)
*G06Q 50/00* (2012.01)
(Continued)

(52) U.S. Cl.
CPC ........... *G01R 33/481* (2013.01); *A61B 5/0035* (2013.01); *A61B 5/055* (2013.01); *A61B 6/037* (2013.01); *A61B 6/5247* (2013.01); *A61B 6/5288* (2013.01); *G01R 33/5673* (2013.01); *A61B 5/0402* (2013.01); *A61B 5/08* (2013.01);
(Continued)

(58) Field of Classification Search
USPC ........................................................ 382/131
See application file for complete search history.

(56) References Cited

U.S. PATENT DOCUMENTS

| 5,800,354 A | 9/1998 | Hofland et al. |
| 6,771,999 B2 | 8/2004 | Salla et al. |

(Continued)

FOREIGN PATENT DOCUMENTS

| JP | 2004509686 A | 4/2004 |
| JP | 2004181246 A | 7/2004 |

(Continued)

OTHER PUBLICATIONS

Klein, G. J., et al.; Real-time System for Respiratory-Cardiac Gating in Positron Tomography; 1998; IEEE Trans. on Nuclear Science; 45(4)2139-2143.

*Primary Examiner* — Neha Patel (57) ABSTRACT

In preparation for acquiring PET image data, subject motion models are built based on physiologic signal monitoring and MR data is collected and used for improved PET imaging. The physiologic signal monitoring is also used during PET imaging, and the acquired MR data is used for prospective or retrospective gating of the PET image acquisition, or in the PET reconstruction for improved correction/imaging.

12 Claims, 3 Drawing Sheets

(51) Int. Cl.

| | | |
|---|---|---|
| *G01R 33/48* | (2006.01) | |
| *A61B 6/03* | (2006.01) | |
| *A61B 6/00* | (2006.01) | |
| *G01R 33/567* | (2006.01) | |
| *A61B 5/055* | (2006.01) | |
| A61B 5/0402 | (2006.01) | |
| A61B 5/08 | (2006.01) | |
| A61B 5/00 | (2006.01) | |
| G01R 33/565 | (2006.01) | |

(52) U.S. Cl.
    CPC ........... *A61B 5/7289* (2013.01); *A61B 5/7292* (2013.01); *A61B 6/541* (2013.01); *G01R 33/5676* (2013.01); *G01R 33/56509* (2013.01)

(56) References Cited

U.S. PATENT DOCUMENTS

| | | | |
|---|---|---|---|
| 7,031,504 | B1 | 4/2006 | Argiro et al. |
| 7,117,026 | B2 | 10/2006 | Shao et al. |
| 8,059,880 | B2 * | 11/2011 | Mizuta et al. ............... 382/131 |
| 2003/0233039 | A1 * | 12/2003 | Shao et al. ................... 600/407 |
| 2005/0226527 | A1 * | 10/2005 | Weese et al. ................ 382/275 |
| 2006/0235295 | A1 | 10/2006 | Boese et al. |
| 2006/0266947 | A1 | 11/2006 | Krieg et al. |
| 2008/0219510 | A1 | 9/2008 | Martin et al. |

FOREIGN PATENT DOCUMENTS

| | | |
|---|---|---|
| WO | 03003796 A1 | 1/2003 |
| WO | 2006111869 A2 | 10/2006 |

\* cited by examiner

MR-PET CYCLIC MOTION GATING AND CORRECTION

CROSS REFERENCE TO RELATED APPLICATIONS

This application claims the benefit of U.S. provisional application Ser. no. 60/986,699 filed Nov. 9, 2007, which is incorporated herein by reference.

The present application finds particular application in subject imaging systems, particularly involving magnetic resonance imaging (MRI) and positron emission tomography (PET). However, it will be appreciated that the described technique may also find application in other imaging systems, other medical scenarios, or other medical techniques.

Several kinds of subject motion can occur during PET and MR scanning, including gross motion of the patient, such as translation and rotation, which can be detected by navigators. In addition, some forms of imaging are relatively immune to motion due to imaging speed or employment of built in corrections, such as propeller (vane) imaging. Fiducials can also be used for registration and/or re-registration for some types of motion, especially if position changes occur between imaging sessions.

Other systems facilitate correction of PET data based on motion detection (e.g., non-repetitive motion) in an integrated system. PET, like single photon emission computed tomography (SPECT), imaging involves injection of a tracer element that is subsequently concentrated by local metabolism and imaged. The imaging process can take tens of minutes, during which the patient may move and of course has continual heartbeat and breathing. The motion detection system is used to image and monitor gross motion to build motion correction/gating into the PET images. However, such systems do not provide motion correction or gating for a tandem MR-PET system. A problem with subject motion during PET acquisition is that the motion blurs the apparent spatial location of tracer accumulation.

MR data acquisition can be synchronized with a monitored physiologic signal to provide stop-action images in a selected phase or frame of a physiological cycle. This is particularly true for cardiac and respiratory gated MR data acquisition. Cardiac motion is usually assumed to follow a regular EKG signal. Respiratory motion is usually derived or associated with a signal from a bellows or monitor attached to the patient. With SENSE coils MR images can often be acquired in a few breath holds. MR navigators may be used to provide a gate/motion signal, however the motion is typically faster than the desired MR image data acquisition time. A series of snapshots can provide an indication of motion over time.

Still other systems calculate motion fields from anatomical images, such as CT images, rather than from direct measurement of displacement, which increases computational overhead and processing time and may have differences between the model and the actual patient motion. Alternatively, multiple high-speed CT images can be employed to build an interpolated motion model, without monitoring motion directly. CT imaging for this purpose would result in additional X-ray radiation dose to the patient, which is a disadvantage.

Often, tissue of interest (e.g., a tumor or the like) does not have the same compression, deformation, and/or motion characteristics as a model constructed using such methods. In these cases, the tissue of interest cannot be accurately modeled without directly measuring its displacement.

The present application provides new and improved PET correction systems and methods that directly measure displacement of a region of interest in a subject, which have the advantages of improving PET image quality and permitting remedial and/or real-time image correction, and which overcome the above-referenced problems and others.

In accordance with one aspect, an imaging system, includes an MR scanner that scans a region of interest in a subject to generate image data of the region of interest during a physiological cycle, and a processor that divides the physiological cycle into a plurality of frames, associates the MR image data to corresponding frames in the physiological cycle, and reconstructs a series of MR images to generate a motion model of the region of interest during the physiological cycle. The system further includes a PET scanner that collects PET data from the region of interest during the frames of the physiological cycle, and a PET reconstruction processor that uses the motion model to generate a PET image in one or more reference frames of the physiological cycle.

In accordance with another aspect, a method of PET imaging includes acquiring MR data of a region of interest in a subject, monitoring a physiological cycle of the subject while acquiring the MR data, associating the acquired MR data to each of a plurality of frames in the physiological cycle, and generating a motion model of the region of interest indicative of region of interest motion relative to each frame. The method further includes monitoring the physiological cycle while collecting PET data during a PET scan, and employing the motion model during reconstruction of the PET data into a motion-corrected PET image in a selected frame of the physiological cycle.

In accordance with yet another aspect, a method of generating a motion-corrected PET image comprises generating a magnetic resonance image corresponding to each of a plurality of frames, including a reference frame, of a physiological cycle, collecting PET data to generate a plurality of lines of response and monitoring the physiological cycle, and associating each line of response with one of the plurality of frames of the physiological cycle. The method further includes adjusting a trajectory of each line of response, outside of the reference frame, in accordance with relative region of interest motion between the MR image corresponding to the same frame and the MR image corresponding to the reference frame, and reconstructing the lines of response with a PET image of the region of interest in the reference frame.

Another aspect relates to a processor configured to execute machine-executable instructions stored on a storage medium, the instructions including acquiring the MR image data of the region of interest in a subject, monitoring a physiological cycle in the subject during MR data acquisition, associating the acquired MR image data with one of a plurality of frames in the physiological cycle, and generating, from the acquired MR data, a motion model indicative of relative displacement of the region of or in interest in each frame. The instructions further include monitoring a physiological signal in the subject during a PET scan, and employing the motion model to infer displacement of the region of interest during each frame of the physiological cycle during the PET scan.

In accordance with another aspect, an imaging system includes a MR scanner that scans a region of interest in a subject to generate images and MR data of the region of interest during a physiological cycle, and a processor that correlates motion during the physiological cycle to the MR images and motion data for the physiological cycle, and characterizes the motion as displacement, relative to a reference position, as a function of time during the physiological cycle. The system further includes a PET scanner that collects PET data from the region of interest during the physiological cycle, and a PET reconstruction processor that uses the motion characterization to generate a PET image at the reference position of the physiological cycle.

One advantage is that image quality is improved.

Another advantage resides in linking MR data to cyclic physiological signal data.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

The systems and methods described herein facilitate using MRI to generate a model of a region of interest of a patient who is to undergo a PET or PET-TOF examination. The model, if displayed as a cine image, would show the motion in the region of interest during a respiratory and/or cardiac cycle and/or other cyclic motion. Each position of the 3D model is keyed to the output of a physiological monitor, such as an EKG and/or respiratory monitor or pulse signal (e.g. PPG). In this manner, the model is generated using direct measurement of displacement of a region of interest (e.g., an organ or structure in the subject). The patient is preferably fitted with the same physiological monitor during the PET data acquisition. Alternately, common physiologic sensors could be used with provision of a second monitor. As each line of response (LOR) is detected, it is recorded with its detection time and with the outputs of the physiological monitor. During image reconstruction, the trajectory of each line of response is positionally corrected in accordance with the MRI generated model. If the organ of interest shifts but does not deform during the cardiac or respiratory cycle, the correction may take the form of a linear offset. If the organ is also partially deformed during the cycle, the correction may be non-linear. Additionally, the MRI model can be used to make dynamic adjustments to the attenuation correction or to dynamically adjust the scatter and stray radiation elimination criteria. It will be appreciated that although various embodiments herein are described with regard to a PET scanner, a SPECT imaging device could also be used.

Figure 1:
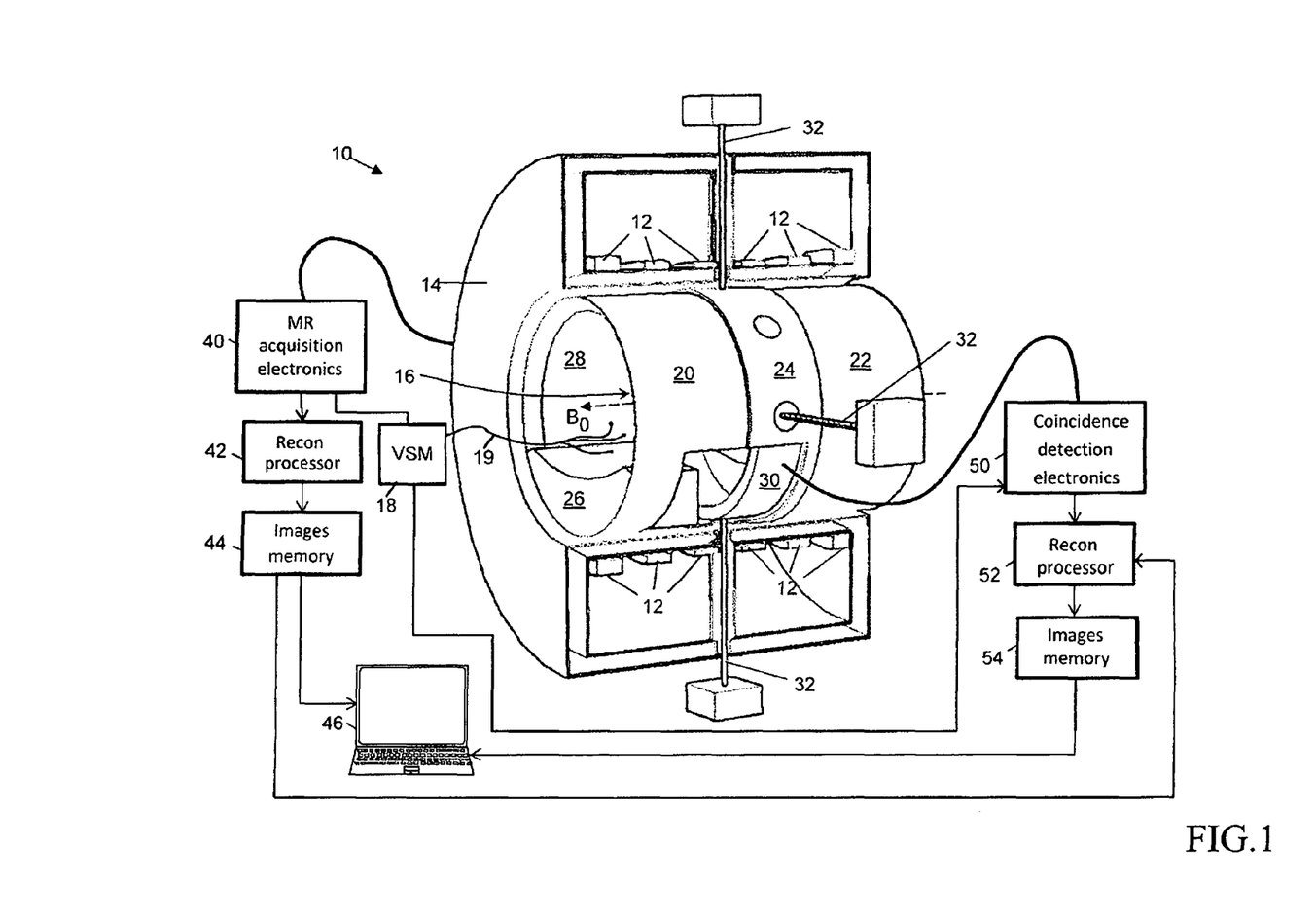
FIG. 1 diagrammatically shows a perspective view of an imaging system with both PET and magnetic resonance imaging capability, and with a vital signs monitor (VSM) that monitors a physiological signal in a subject. The illustration includes one VSM but may include two separate VSMs in an alternate embodiment, wherein preferentially the sensors/leads are common.

With reference to FIG. 1, an imaging system 10 includes a combined PET-MR scanner, although separate scanners are also contemplated. The MR portion includes main magnet windings 12 disposed in a cryogenic housing 14 defining a main magnet producing the static axially oriented $B_0$ magnetic field in a magnetic resonance examination region 16. Magnetic field gradient coils 20, 22 (diagrammatically shown as supportive formers without depicting the magnetic field gradient-generating conductors) are constructed in two parts with an annular gap therebetween that is bridged by a mechanical brace 24 to accommodate Lorentz forces between the gradient coil portions 20, 22. The magnetic field gradient coils may include separate resistive shim coils, e.g. second order resistive shims, for the purpose of altering the main magnetic field homogeneity. The illustrated magnetic resonance scanner is a bore-type scanner and includes a subject support 26 that provides mechanical support for a separate tabletop (not shown) that moves into the bore to support a subject, such as a human medical patient, at or near a central axis of the bore. In some embodiments, a generally whole-body RF transmit/receive coil 28 may be disposed inside the gradient coils along the bore. The central annular gap is, in the embodiment of FIG. 1, free of gradient coil windings, except possibly for current feed conductors (not shown) that optionally cross the central gap to electrically connect the two sub-sets 20, 22 of magnetic field gradient coil windings. Each portion 20, 22 includes primary gradient coil windings supported on an inner cylindrical surface of the formers 20, 22, and shield gradient coil windings supported on an outer cylindrical surface of the formers 20, 22, and optionally also connecting conductors disposed at each edge of the central annular gap that electrically connect selected primary and secondary coil windings.

The system 10 also includes a vital signs monitor (VSM) 18 and leads 19 that are coupled to a subject during MRI and/or PET scans. According to one embodiment, the VSM is an electrocardiograph (ECG or EKG) device that monitors cardiac cycles. In another embodiment, the VSM is a respiratory monitor that measures respiratory rate or other parameters associated with subject respiration. The VSM may also be used to monitor pulse. In another embodiment, both cardiac and respiratory cycles are measured. In any case, the VSM monitors one or more cyclic events in the subject (e.g., heartbeat, respiration, etc.) while the subject undergoes an MR data acquisition, and each k-space data line detected by the MR scanner is timestamped and recorded with the output of the VSM.

For example, in a given heartbeat cycle, one or more MR k-space data lines may be detected during an atrial contraction, recorded as such, and marked with respective timestamp. A second group of data lines may be detected during a ventricular contraction, recorded as such, and marked with respective timestamps. By associating or sorting the k-space data lines with a physiological event and a timestamp, complete MR data sets corresponding to each of a plurality of phases or frames of the monitored physiological cycle(s) can be generated. Reconstruction of these data sets generates a series of images or models that describe the anatomy of the imaged region during each of the physiological phases or frames. It will be appreciated that the foregoing example is illustrative in nature and that the systems and methods described herein are not limited to monitoring contractions of a heart or portions thereof.

An annular ring or band of positron emission tomography (PET) detectors 30 are disposed in an annular central gap of the magnetic field gradient coil 20, 22. The PET detectors 30 are supported mechanically in a thermally and vibrationally isolated manner from the support of the magnetic field gradient assembly 20, 22, 24. In the illustrated embodiment, mounting members 32 pass through the openings in the brace 24 and openings in the cryogenic magnet housing 14 to support the annular ring of PET detectors 30 independently from the magnetic field gradient assembly 20, 22, 24.

Such independent support is advantageous because the gradient coil assembly 20, 22, 24 generally distorts and vibrates during operation due to Lorentz forces. One option not illustrated is to mount the PET electronics with active or passive vibration isolation to the bore of the magnet independently of the gradient coil. The outer support (not shown) to which the mounting members 32 connect can be a sub-frame completely surrounding the magnetic resonance scanner, a set of hard points on the walls of the room containing the scanner, a vibration isolation mount to the surface of the magnet's outer structure, or so forth.

With continuing reference to FIG. 1, the magnetic resonance scanner further includes acquisition electronics 40 that operate the magnetic field gradient coil 20, 22 and one or more radio frequency coils 28 to generate and collect k-space data samples that are processed by a reconstruction processor 42, such as a fast Fourier transform (FFT) reconstruction processor to generate a series of 2D or 3D magnetic resonance images in each of the physiological phases or frames that are stored in an images memory 44, displayed on a user interface 46, or otherwise utilized. The acquisition electronics 40 may also control the timing and level of electric current supplied to resistive shim coils (not shown) that are used to alter the main magnetic field homogeneity within the subject.

The PET detectors 30 are controlled by coincidence detection electronics 50 to identify and accumulate substantially coincident 511 keV gamma ray detection events indicative of positron-electron annihilation events in an examination region surrounded by the annular ring of PET detectors 30. Although the coincidence detection electronics 50 are illustrated as a discrete unit in FIG. 1, it is contemplated for a portion of these electronics to be integrated with the PET detectors 30. For example, the PET detectors 30 may be silicon photomultiplier (SiPM) detectors formed on silicon substrates that also support analog-to-digital conversion electronics and time-stamping electronics such that the data offloaded from the PET detectors 30 comprises digitally timestamped digital samples corresponding to radiation detection events, for example in a list format.

The remote portion of the coincidence detection electronics in such an embodiment include digital data processing electronics that search the list of digital samples for radiation detection events that are coincident within a selected time window and have energies corresponding to gamma rays within a selected energy window. The substantially coincident detection events define endpoints of a line of response, somewhere along which occurred the sourcing positron-electron annihilation event that produced two 511 keV gamma rays. The lines of response are also stamped with the corresponding time of the physiological cycle either at the detector 30 or as loaded into the coincidence detection electronics.

In some embodiments, the coincidence detection electronics 50 acquire time-of-flight (TOF) PET data, in which a time difference (or lack thereof) between the two substantially coincident 511 keV gamma ray detection events are used to at least approximately localize the sourcing positron-electron annihilation event along the line of response. For example, if the time difference is zero, then the sourcing positron-electron annihilation event is localized to about the midpoint of the line of response. On the other hand, if the time difference is large (e.g., of order 500 ps), then the sourcing positron-electron annihilation event is localized to be closer to the detector of the earlier of the two substantially coincident 511 keV gamma ray detection events. For either PET or TOF-PET data, a reconstruction processor 52 performs an image reconstruction process, such as an iterative maximum-likelihood expectation maximization reconstruction, to generate PET images that are stored in an images memory 54, displayed on a user interface 46, or otherwise utilized. As described below, the trajectory of each LOR or the image space into which it is projected is altered in accordance with the multiple 2D or 3D MR images or model depicting the same phase or frame of the physiological cycle(s).

Rapid MR imaging can be used to estimate motion as a function of time relative to a physiologic signal reference detected by the VSM 18. In one embodiment, the MR imaging purpose differs from that of diagnostic imaging, focusing on motion model construction rather than imaging per se. Thus, MR imaging tradeoffs can be made such the image acquisition time is optimized for motion model building with the constraint of adequate spatial resolution. For example, physiological cycles often have one or more frames or phases that are temporally short, and one or more frames or phases that last longer. The data acquisition order is adjusted on-the-fly in accordance with the physiological signal from the VSM to assure adequate data sampling in each phase, while minimizing over-sampling.

In general the monitored changes and/or motions are also faster than the PET acquisition time. In these cases, it is useful to have a patient or object motion model built from the MR images based on (e.g., relative to) a monitored physiologic signal. An approximate relationship between subject motion and time, relative to a physiologic signal reference, is established from acquired MR images. This motion model is used to correct or select the PET acquisition intervals, and then correct the PET images, which provides improved correlation between the MR and PET images as well as positional data to correct PET images based on MR image motion models. Depending on the illness, patients are sometimes monitored while being imaged as a matter of patient safety. This is commonly done with a breathing monitor and/or a cardiac monitor (e.g., the VSM). Patient monitors can also be used for prospective or retrospective gating to improve imaging (e.g., synchronization of acquisition with the patient motion). Even if medical monitoring is not performed, the MR system is equipped with the basic hardware required to obtain a physiologic signal for gating, such as respiratory, PPG and/or EKG signals. This hardware is not classified as a monitoring system but provides useful signals for reference and for the performing the various functions described herein.

In a tandem PET-MR system, repetitive/cyclic patient motion can be time-course characterized and/or modeled while imaging in the MR system. This motion modeling may then be used to enhance the PET imaging in several manners. For instance, patient motion characterization is performed by rapid MR imaging and time referenced storage of at least one of cardiac, pulse, breathing, or other physiologic signals while in the MR system. A 2D or 3D model of the patient motion corresponding to the physiologic signal monitoring measurements is then constructed from the MR images. In one embodiment, boundary and specific organ motion vs. time correlations are established. Continued physiologic signal monitoring during the PET imaging can then be used for selecting appropriate acquisition intervals (e.g., prospective or retrospective gating) for motion correction. The physiologic signal monitoring is based on the same physiologic signal type(s) used to establish the motion model from MR data. Although the following examples are described with regard to a tandem PET-MR system, the approach can also be used in an integrated system or with a PET insert in an MR system. Additionally, although the system of FIG. 1 relates to an integral PET-MR system, separate PET and MR devices can be employed in conjunction with various aspects described herein.

According to one embodiment, breathing is monitored as an expansion of the chest. The motion of the diaphragm and organs close to it, such as the lungs, kidneys, liver, etc., can occur predominantly in the head/foot direction. MR imaging can be used to construct 3D and/or multi-slice 2D models over this cycle based on the monitored physiologic signal. The MR acquisition can be synchronized to the physiologic signal and the physiologic signal is digitized and stored for reference to build a motion vs. time model, where time is referenced to an arbitrary or selected starting point (or phase) in the physiologic signal acquisition. These numerical models are then used to correct and/or gate the PET images accordingly for better images by using the same physiologic condition(s) to time register the acquisition of the PET scan. When the PET acquisition is started, a corresponding point (or phase) in the physiologic signal temporal profile is known from the VSM. The physiologic signal time course (e.g., cycle frame or phase) is measured and stored during the PET acquisition. With the established subject motion vs. time model, a cyclic motion model is thus constructed, stored, and employed during the PET acquisition to allow spatial correction of the PET data. In order to effectively time register the separate PET and MR acquisitions a correlation function or other methods may be used to determine an optimum alignment of the two separate physiological signal streams (or time series).

Cardiac monitoring and/or gating is also useful for heart imaging. The MR image with gating can be used to characterize and model the positions of the heart over the cycle. This model can then be used to gate or correct the PET cardiac images accordingly. The MR motion model can be established on a per subject basis. An MR training or model building phase, in parallel with physiologic signal acquisition, is thus performed prior to the PET scan.

In other embodiments, the VSM includes an ultrasound device for diaphragm tracking, and/or a device for monitoring simple blood pressure pulses for cardiac monitoring.

Where motion of the patient boundary is of particular interest an MR data set may be acquired that is gated to a single phase of the physiologic signal of interest. This data should provide a reasonable snapshot of the patient boundary at one particular phase. This may be followed by a series of rapid anterior-posterior (A-P) and left-right (L-R) MR projections to measure the dimensions of the patient boundary in these two directions throughout various phases of the physiologic signal cycle. A motion model could then be used to expand and contract the patient boundary of the snapshot image set for other phases of the physiologic signal based on the obtained projection data. A 1D transform of the zero-phase encode view in each of A-P and L-R directions may be used for this purpose.

Figure 2:
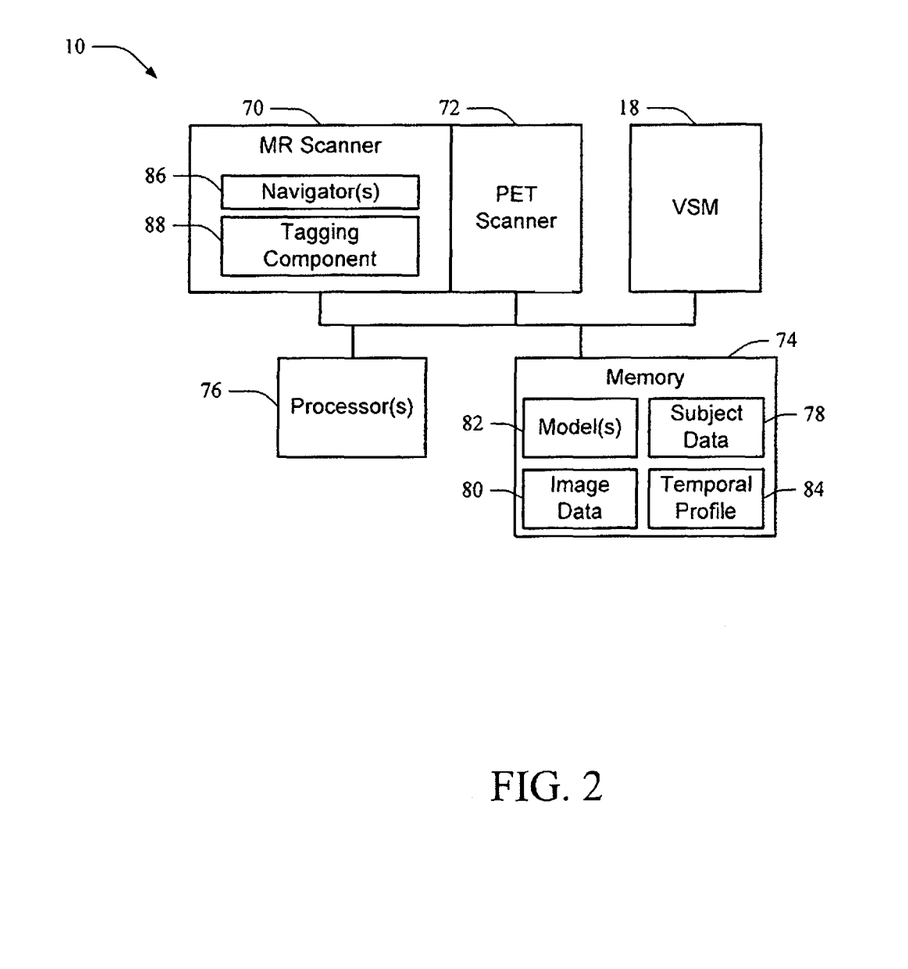
FIG. 2 illustrates another embodiment of the system for performing PET image correction using a motion model generated from an MR scan in conjunction with a signal reference measured by a VSM.

FIG. 2 illustrates another embodiment of the system 10 for performing PET image correction using a motion model generated from an MR scan in conjunction with a signal reference measured by a VSM 18. The system includes an MR scanner 70, which may be integral to or separate from a PET scanner 72. It will be appreciated that although various embodiments herein are described with regard to a PET scanner, a SPECT imaging device could also be used. The VSM, MR scanner, and PET scanner are coupled to memory 74 that stores a variety of information, and processor(s) 76 that execute one or more machine-executable algorithms for analyzing, manipulating and/or processing information stored in memory 74. The processor 76 time-stamps the physiological signals acquired during MR and PET scans, and time-registers the physiological signals acquired during the PET scanning to the physiological signals acquired during the MR scan using a correlation function to align the physiologic signals acquired during MR and PET scanning. The time-stamped physiological signals and registrations are digitally stored to memory 74.

In one embodiment, the memory 74 stores subject data 78 related to one or more monitored signals (e.g., heart rate, ECG data, respiration cycles, etc.), as well as image data generated by one or both of the MR scanner and the PET scanner. The memory additionally stores one or more motion models 82 generated by the processor from the subject data, MR image data, and a temporal profile 84, which is generated from the subject data. For instance, the temporal profile can include a timeline of events in a cardiac cycle, a respiratory cycle, or the like. The processor(s) 76 include algorithms for time registering the two separate physiologic signal sets using correlation function or other methods.

The PET scanner 72 can acquire and store data in a "list mode," which is a selected time ordered list of detection events that may be used for a reconstruction. The temporal profile is generated to include a data record containing time and position of events in the detector array so as to define a "line of response" between temporally adjacent events. The time stamps can further define a distribution for the likely origin of the positron along this line. Gating is performed by selecting events that occur when the object is in a known position or state that is inferred from a physiologic or other signal source. Selecting a range of positions for a gated acquisition is performed by selecting appropriate time intervals. For instance, a motion model generated using a physiological signal cycle divided into 10 frames may show that frames 3 and 7 correspond to periods of relatively low motion, and are thus desirable periods during the physiological signal cycle to scan using a PET scanner.

In a more general case where all collected data is employed, object motion can be predicted. For instance, patient motion can be measured directly or predicted from a model to determine $x(t)$, $y(t)$, and $z(t)$ of a region of interest or the like. The list mode format of acquisition and event selection for reconstruction facilitates time registering object motion and PET acquisition. Consequently, if a reference object position (e.g., a reference frame or phase of the physiological cycle) is selected, the PET event can be displaced to the reference position using vector displacement over time and a maximum use of available data is made to build the image. If one chooses, one could use a series of reconstructions at different reference positions and view the PET event activity over the motion cycle.

According to an example, one-dimensional or translational motion imaging near the diaphragm (or the base of the lung or top surface of the liver) is performed. The motion may be described by $z(t)$ with $x(t)=y(t)=0.0$ for all t. In this example, "hotspot" PET events can be properly repositioned in time based on the model or measurement from the list mode to a reference position. Alternatively, the events could be accumulated in several frames (e.g., 10 or so) based on the MR model. Knowing the translational position of each frame, the frames are then shifted to provide an aligned hotspot composite image. One advantage of cyclic motion correction is that the use of the event statistics is maximized as compared to a gated study, which only uses the fraction of the events that occur in the selected frame(s).

The MR scanner 70 generates one or more navigator sequences 86 that measure displacement of an organ or anatomical structure with MR signals. For instance, the navigators can be employed for gating MRI data acquisition (e.g., where gating includes selecting events that occur when the object is in a known or inferred position, as described above). Additionally, the navigators can measure motion relative to an external monitor. According to an example, a sensitive volume (e.g., 2 cm×2 cm×40 cm, or some other volume) is excited in the patient by the operator. If the long dimension is in the diaphragm motion direction, a 1D Fourier transform of the signal shows where an object(s) (e.g., a diaphragm) is located. Each repetition of the navigator sequence shows the current position. If boundaries are of interest, a derivative defines boundaries over time. When the region of interest is farther from the moving boundary (e.g., the diaphragm in this example) the model can be two-dimensional or three-dimensional. The navigator can be preferentially oriented to follow the maximum displacement. In other embodiments, the navigator(s) 86 include rotational navigators that measure rotation of a region of interest as the subject moves.

When subject motion is relatively rapid or complex, the MR scanner can employ a tagging component 88, which generates tagging sequences to describe motion of an organ. For instance, cardiac tagging sequences can be employed to describe motion of the heart. Cardiac tagging uses a sequence that applies a series of saturation bands to the heart. In the two dimensional case, the sequence is a square grid of saturation bands. The bands are dark (e.g., lines of no or minimal MR signal) criss-crossing the image. Imaging then shows distortion of the heart (or other object) between the time the tag was applied and the time of readout of the image. Time sequential frames can thus be registered with this technique. Such tagging techniques can also be employed to show motion of lungs (lung boundaries in particular), and the sequences can be one, two, or three dimensional. The tagging component can track each grid position signal and assign a vector displacement thereto. In this manner special organ segmentation methods to create the motion model are avoided. The motion of voxels located outside of the saturation grid can be inferred using interpolation or other methods. In one embodiment, the MR model 82 is a pixel-by-pixel (or voxel-by-voxel) parametric model, which accurately describes the position and velocity of each pixel at any time. This parametric model can then be used to accomplish the motion corrections described above.

MR spin tagging sequences encode saturation bands onto selected parts of tissue. Using this process one can follow and measure the motion of specific tissue. This may be advantageous with complex motion, inelastic materials and the like. In this case the motion characterization is not based on a model from static images but is an actual measurement of motion of selected tissue. Likewise, the motion of an excited selected voxel as in spectroscopy could be imaged to create a motion model on a smaller scale. This latter method may be more appropriate to track liver motion due to respiration. In both of these cases there is an excitation (reference) and readout position with time evolved motion in between the two. Both of these methods allow for the direct measurements of displacements of the excited regions as the tissue moves. These direct measurements can be used for correcting for motion at similar time points in a physiological signal that is acquired and digitized simultaneously to the acquisitions.

Figure 3:
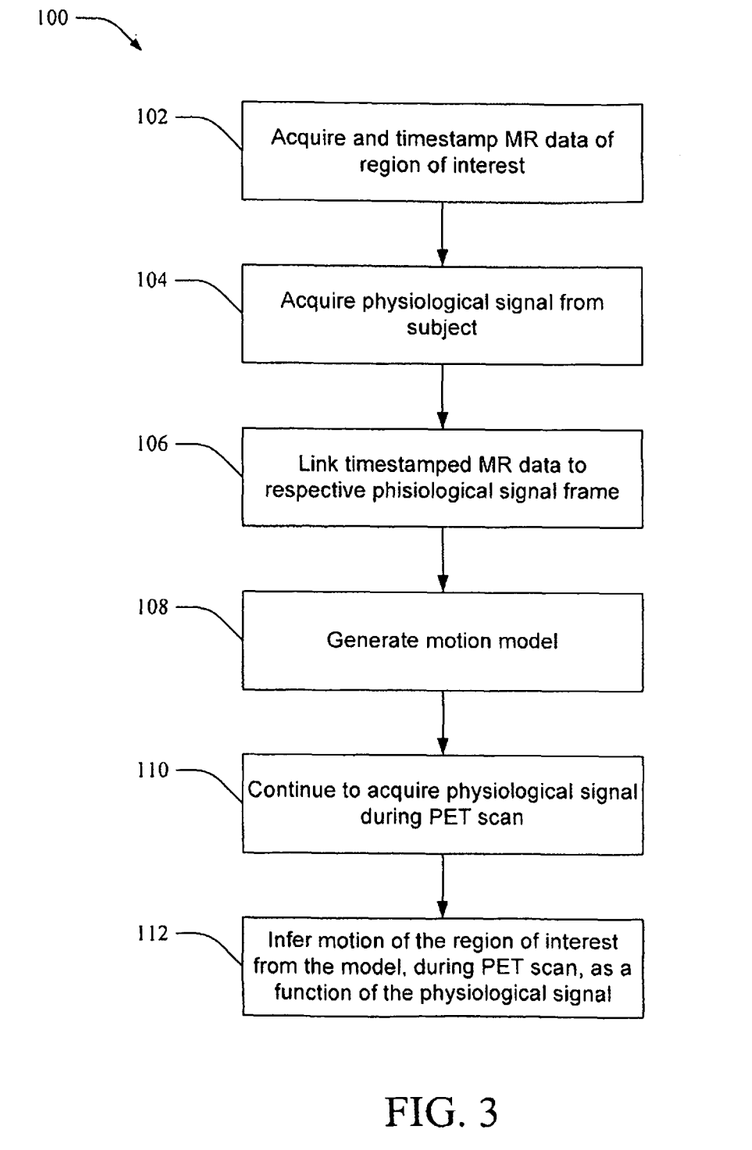
FIG. 3 illustrates a method for generating a motion model using a monitored reference signal and MR scan data, and employing the motion model for PET scan image data correction.

FIG. 3 illustrates a method 100 for generating a motion model using a monitored reference signal and MR scan data, and employing the motion model for PET (or SPECT) scan image data correction. At 102, a region of interest (e.g., an organ or anatomical structure in a subject) is scanned using an MR scanner, and the MR k-space data lines are time-stamped as they are detected. Concurrently, a physiologically signal (e.g., heartbeat, ECG, respiration, etc.) is monitored in the subject, and partitioned into frames or phases, at 104. For example, a cardiac cycle, such as a complete heartbeat, can be divided into a number of frames or phases (e.g., 2, 5, 10, etc). Timestamped MR data is linked to a corresponding frame in a temporal profile describing a cycle of the physiological signal, at 106. For instance, MR data that is detected during first frame of a cycle is marked as such, and MR data detected during a second frame is indicated as having been detected during the second frame, and so on. The steps 102, 104, 106 may be repeated to acquire sufficient MR data to reconstruct and image associated with each frame or phase of the physiologic signal. At 108, a motion model is generated as a function of the detected MR data and the physiological signal. That is, a time-dependent model is generated with slightly different shapes corresponding to different frames in the physiological signal cycle. For example, the MR data from each frame is reconstructed into a corresponding image. The images provide a model for each frame of the location, shape, etc., of organs and tissue structure in the region of interest. At 110, a PET (or SPECT) scan is performed on the region of interest, while monitoring the physiological signal. At 112, motion of the region of interest is inferred as a function of a current point or frame in the monitored physiological signal cycle. For instance, as the physiological signal proceeds through a cycle, at each frame therein, the MR model is employed to predict a deformation of the region of interest, which is then used to correct the PET (or SPECT) image. In another embodiment, the motion model is employed to identify appropriate PET (or SPECT) scan periods, such as during frames in the signal cycle during which motion is minimal as determined from the MR scan data. In this manner, the method facilitates correcting PET (or SPECT) image data for inaccuracies associated with cyclical subject motion, which can improve image appearance, reduce blurred image representations, etc.

One way to visualize this correction is to consider the reconstructed PET image as a rectangular array of voxels corresponding to the imaged region. Due to the cyclic motion, the organ(s) of interest is moving relative to the array of voxels. If the lines of response are back-projected from different frames into the voxel array, blurring will occur.

The MR image in each frame can be described as a like array of voxels (although the voxels can be smaller to increase accuracy). The MR images can be 1D images (e.g., from navigator sequences), 2D images, or 3D images. As used herein, "images" denotes image representations that are readable by a computer and does not require that the image be converted into a human-readable image for display.

To reconstruct a PET reference frame, each line of response in the reference frame is simply back-projected into the PET voxel array. For each line of response collected in a frame other than the reference frame, one looks to the MR image of the same frame. By comparing how the organ(s) of interest in the same-frame MR image has moved relative to the reference MR frame image, one can determine how the trajectory of the line of response needs to be adjusted to define the corresponding trajectory through the organ(s) of interest in the reference frame. Stated more mathematically, a transform is determined to transform the trajectory of the LOR through the organ(s) of interest in the non-reference frame MR image to the same trajectory relative to the organ(s) of interest in the reference frame MR image. The line of response is adjusted (transformed) accordingly and back-projected into the PET image voxel array.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. An imaging system, including:
a magnetic resonance (MR) scanner that scans a region of interest in a subject to generate image data of the region of interest during a physiological cycle;
a processor that divides the physiological cycle into a plurality of frames, associates the MR image data to corresponding frames in the physiological cycle, and reconstructs a series of MR images to generate a motion model of the region of interest during the physiological cycle;
a positron emission tomography (PET) scanner that collects PET data from the region of interest during the frames of the physiological cycle;
a PET reconstruction processor that uses the motion model to generate a PET image in one or more reference frames of the physiological cycle; and
a vital signs monitor (VSM) that monitors the physiological cycle in the subject as the MR scanner scans the region of interest;
wherein the processor analyzes the motion model to determine an amount of detected motion in each frame of the cyclic physiological signal, identifies a frame in which a smallest amount of motion occurred during the MR scan, and gates the PET scanner to collect data during the identified frame.

2. The system according to claim 1, wherein the PET scanner collects data from the region of interest as lines of response in list mode, and marks each line of response in accordance with the frame in which it is collected.

3. The system of claim 1, wherein the PET scanner is a time-of-flight (TOF) scanner.

4. The system according to claim 1, wherein the VSM includes at least one of an electrocardiograph to monitor a cardiac cycle in the subject and a respiratory monitor to monitor a respiratory cycle in the subject.

5. The system according to claim 1, wherein the VSM monitors the cyclic physiological signal in the subject during the PET scan.

6. The system according to claim 1, wherein the PET reconstruction processor adjusts PET data collected during a frame other than the reference frame in accordance with the motion model and reconstructs the adjusted PET data into a PET image corresponding to the reference frame.

7. The system according to claim 6, wherein the MR scanner generates navigator sequences that generate MR image data that is reconstructed to indicate at least one of displacement of the region of interest relative to a predefined point, and
rotation of the region of interest relative to a predefined axis.

8. The system according to claim 6, wherein the motion model is a 3D model of the region of interest.

9. The system according to claim 1, wherein the processor includes:
a routine for acquiring the MR image data of the region of interest in a subject; a routine for monitoring a physiological cycle in the subject during MR data acquisition;
a routine for associating the acquired MR image data with one of a plurality of frames in the physiological cycle;
a routine for generating, from the acquired MR data, a motion model indicative of relative displacement of the region of interest in each frame;
a routine for monitoring a physiological signal in the subject during a PET scan; and
a routine for employing the motion model to infer displacement of the region of interest during each frame of the physiological cycle during the PET scan.

10. An imaging system, including:
a magnetic resonance (MR) scanner that scans a region of interest in a subject to generate images and MR data of the region of interest during a physiological cycle;
a processor that correlates motion during the physiological cycle to the MR images and motion data for the physiological cycle, and characterizes the motion as displacement, relative to a reference position, as a function of time during the physiological cycle;
a positron emission tomography (PET) scanner that collects PET data from the region of interest during the physiological cycle; and
a PET reconstruction processor that uses the motion characterization to generate a PET image at the reference position of the physiological cycle.

11. The system according to claim 10, wherein the motion characterization includes a measurement of motion of selected tissue using an MR spin tagging technique.

12. The system according to claim 10, wherein the processor timestamps the physiological signals acquired during MR and PET scans, and time-registers the physiological signals acquired during the PET scanning to the physiological signals acquired during the MR scan using a correlation function to align the physiologic signals acquired during MR and PET scanning, and wherein the time-stamped physiological signals and registrations are digitally stored to memory.

* * * * *